(12) United States Patent
Eberhardt et al.

(10) Patent No.: US 9,566,413 B2
(45) Date of Patent: Feb. 14, 2017

(54) DILATOR CENTERING DEVICE AND ASSEMBLIES

(75) Inventors: Mark Eberhardt, Elverson, PA (US); Hiroyoshi Ise, Bear, DE (US); George Stern, Newark, DE (US); Michael Miller, Baltimore, MD (US); Yasutake Yamada, Bear, DE (US); Husexin Fertac Bilge, Chesapeake City, MD (US)

(73) Assignee: TERUMO MEDICAL CORPORATION, Somerset, NJ (US)

( * ) Notice: Subject to any disclaimer, the term of this patent is extended or adjusted under 35 U.S.C. 154(b) by 42 days.

(21) Appl. No.: 13/428,901

(22) Filed: Mar. 23, 2012

(65) Prior Publication Data

US 2013/0253563 A1 Sep. 26, 2013

(51) Int. Cl.

| A61M 29/00 | (2006.01) |
| A61M 25/00 | (2006.01) |
| A61M 25/01 | (2006.01) |
| A61M 39/22 | (2006.01) |

(52) U.S. Cl.
CPC ......... *A61M 25/0097* (2013.01); *A61M 25/01* (2013.01); *A61M 29/00* (2013.01); *A61M 39/22* (2013.01)

(58) Field of Classification Search
CPC ...... A61M 39/22; A61M 39/06; A61M 29/00; A61M 25/0097; A61M 25/0014; A61M 25/01; A61M 2029/025; A61B 1/32; A61B 2039/0626
USPC ... 606/108, 184, 185; 600/184; 13/108, 184, 13/185
See application file for complete search history.

(56) References Cited

U.S. PATENT DOCUMENTS

| 4,798,594 | A | * | 1/1989 | Hillstead .................. 604/167.04 |
| 4,895,565 | A | * | 1/1990 | Hillstead .................. 604/167.04 |
| 5,064,416 | A | * | 11/1991 | Newgard et al. ........ 604/167.03 |
| 5,114,408 | A | * | 5/1992 | Fleischhaker et al. .. 604/167.04 |
| 5,391,152 | A | * | 2/1995 | Patterson ................. 604/165.04 |
| 5,520,655 | A | * | 5/1996 | Davila et al. ............ 604/167.04 |
| 5,807,338 | A | * | 9/1998 | Smith et al. ............. 604/164.01 |
| 6,712,791 | B2 | * | 3/2004 | Lui et al. ................. 604/167.04 |
| 6,719,772 | B2 | * | 4/2004 | Trask et al. .................... 606/191 |
| 6,722,705 | B2 | * | 4/2004 | Korkor ......................... 285/332 |
| 7,744,571 | B2 | * | 6/2010 | Fisher et al. ............ 604/167.04 |
| 2003/0088264 | A1 | * | 5/2003 | Spohn et al. ................. 606/194 |
| 2004/0127772 | A1 | * | 7/2004 | Ewers et al. .................. 600/212 |

(Continued)

OTHER PUBLICATIONS

Australian Office Action for Australian application No. 2013201637, Oct. 27, 2016, 3 pages.

*Primary Examiner* — Julie A Szpira

(57) ABSTRACT

The present technology is directed to a dilator centering device and assemblies and methods using same. In particular, a dilator centering device in accordance with the disclosed technology can be used with a sheath hub assembly. In one embodiment, a dilator centering device includes a lumen capable of receiving a dilator shaft and centering a dilator shaft with respect to the sheath hub as the dilator shaft enters the sheath hub. In one embodiment, the dilator centering device can be attached to the sheath hub during manufacturing or it can be attached at the use site. In one embodiment, the dilator centering device can be integrated with and non-removable from the sheath hub. The embodiments disclosed herein are illustrative and do not limit the scope and spirit of the disclosed technology.

25 Claims, 22 Drawing Sheets

(56) References Cited

U.S. PATENT DOCUMENTS

| | | | |
|---|---|---|---|
| 2004/0181273 A1* | 9/2004 | Brasington et al. | 623/1.15 |
| 2009/0076464 A1* | 3/2009 | Gresham | A61B 17/3498 604/264 |
| 2010/0204660 A1* | 8/2010 | McKinnon et al. | 604/244 |
| 2012/0283640 A1* | 11/2012 | Anderson et al. | 604/164.1 |
| 2014/0319393 A1* | 10/2014 | Thome | 251/147 |

\* cited by examiner

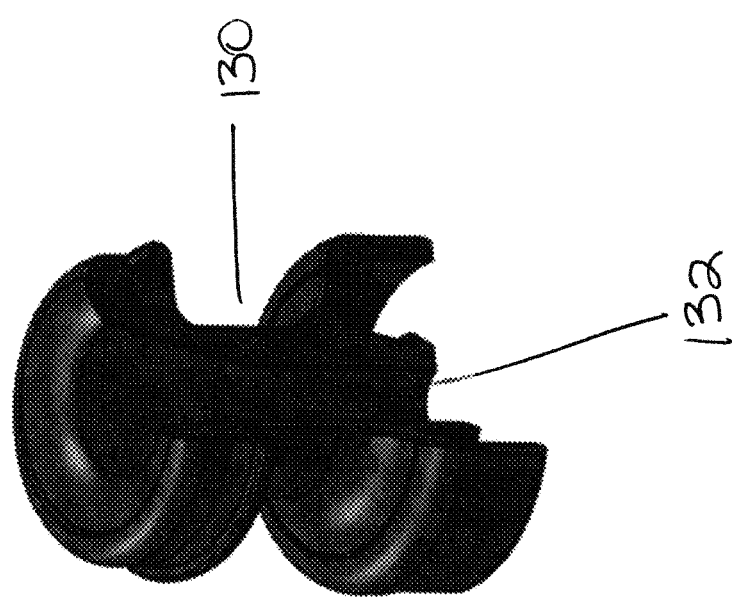

DILATOR CENTERING DEVICE AND ASSEMBLIES

BACKGROUND OF THE TECHNOLOGY

The present technology is related to the field of medical and industrial instruments used for access to a cavity or lumen and more specifically, in one embodiment, to vascular access within the body of a patient.

In today's medical field, many medical procedures require entry into a patient's blood or other vessel for purposes of accessing a desired treatment site, i.e. surgical, treatment, diagnostic. In order to gain access to the desired site, a sheath is usually advanced through the vessel. Once in place within the patient's vessel, various types of medical instrumentation can be fed through the sheath and positioned at the desired site so that the procedure may be performed.

To initially gain access to a particular site within a patient, a needle is used to puncture the patient's skin and gain entry to a desired blood vessel (blood vessel is used throughout for convenience and only as an example of different vessels that may be accessed). A guide wire is then inserted into a lumen in the needle and is fed into the blood vessel. The needle is then removed, with the guide wire being left in place.

A dilator/sheath assembly is then placed over the guide wire and advanced to a position inside the blood vessel. Once the guide wire and the dilator/sheath assembly are advanced within the blood vessel to the desired site, the dilator is removed. The guide wire and sheath are now used to introduce and guide medical instrumentation to the desired site.

As the above procedure is performed within a patient's body, instrument integrity is of concern. Malfunctioning or damaged instruments may, for example, cause tissue trauma, introduce unintended contaminants into a patient's body, or result in leakage of fluids. Accordingly, research and development for improving the integrity of medical instruments is an area of ongoing concern in the medical field.

SUMMARY OF THE TECHNOLOGY

The present technology is directed to a dilator centering device and assemblies and methods using same. The embodiments disclosed herein are illustrative and do not limit the scope and spirit of the disclosed technology.

In one aspect of the disclosed technology, a device is disclosed, for use with a dilator that includes a proximal structure, a distal structure, and a center structure. The proximal structure is configured to engage a dilator and has a first opening capable of receiving a dilator shaft of the dilator. The distal structure is configured to engage a sheath hub and has a second opening capable of receiving the dilator shaft. The center structure connects to the proximal structure and the distal structure and includes a lumen interposed between the first opening and the second opening, wherein the lumen is narrower than the first opening and is capable of receiving the dilator shaft, and wherein the lumen is capable of substantially centering the dilator shaft with respect to the sheath hub as the dilator shaft enters the sheath hub.

In one embodiment, the distal structure is configured to engage the sheath hub by a releasable locking mechanism. In one embodiment, the releasable locking mechanism includes an inner stem surrounding the second opening that is configured to fit into the sheath hub and one or more flanges around the inner stem configured to removably engage an outer surface of the sheath hub.

In one embodiment, the device further includes the sheath hub. In one embodiment, the sheath hub is engaged with the releasable locking mechanism of the distal structure. In one embodiment, the sheath hub is non-removably engaged with the distal structure. In one embodiment, the proximal structure, the centering structure, and the distal structure are each configured to come apart when a threshold force is applied to the proximal structure.

In one embodiment, the proximal structure is configured to engage the dilator by a locking mechanism configured to engage a dilator hub of the dilator. In one embodiment, the locking mechanism is a circumferential groove on an outer surface of the proximal structure.

In one embodiment, the device further includes a seal within the lumen that spans a portion of the lumen or can span the entire lumen or beyond. In one embodiment, the seal is a funnel seal, a spiral funnel seal, a spiral double-funnel seal, a multiple hinged flap seal, or a multiple hinged spiral-flap seal. In one embodiment, the seal has at least three flaps.

In one aspect of the disclosed technology, an apparatus is disclosed that includes a dilator, a sheath hub, and a dilator centering device engaged with the sheath hub. The dilator includes a dilator hub and a dilator shaft connected to the dilator hub. The sheath hub is capable of receiving the dilator shaft. The dilator centering device includes a lumen capable of receiving the dilator shaft, wherein the lumen is capable of substantially centering the dilator shaft with respect to the sheath hub as the dilator shaft enters the sheath hub.

In one embodiment, the dilator centering device is engaged with the sheath hub by a releasable locking mechanism. In one embodiment, the releasable locking mechanism includes an inner stem configured to fit into the sheath hub and one or more flanges around the inner stem configured to removably engage an outer surface of the sheath hub. In one embodiment, the dilator centering device is non-removably engaged with the sheath hub.

In one embodiment, the dilator centering device is configured to engage the dilator hub by a locking mechanism. In one embodiment, the locking mechanism is a circumferential groove on an outer surface of the dilator centering device. In one embodiment, the apparatus further includes a seal within the lumen that span a portion of the lumen or can span the entire lumen or beyond. In one embodiment, the seal is a funnel seal, a spiral funnel seal, a spiral double-funnel seal, a multiple hinged flap seal, or a multiple hinged spiral-flap seal. In one embodiment, the seal has three or more flaps.

In one aspect of the disclosed technology, a method of operating a dilator and a sheath hub is disclosed. The dilator has a dilator hub and a dilator shaft. A dilator centering device includes a lumen capable of receiving the dilator shaft and substantially centering the dilator shaft with respect to the sheath hub as the dilator shaft enters the sheath hub. The method includes attaching a dilator centering device to a sheath hub, and inserting the dilator shaft through the lumen into the sheath hub until the dilator hub engages the dilator centering device. The method includes disengaging the dilator centering device from the sheath hub while the dilator hub is engaged with the dilator centering device, and removing the dilator shaft from the sheath hub.

In one aspect of the disclosed technology, the method includes attaching a dilator centering device to a sheath hub, inserting the dilator shaft through the lumen into the sheath hub until the dilator hub engages the dilator centering device, applying force at the dilator hub to the dilator centering device until the dilator centering device comes apart and disengages from the sheath hub, and engaging the dilator hub with the sheath hub.

In one aspect of the disclosed technology, the method includes accessing a dilator centering device that is non-removably attached to a sheath hub, and inserting the dilator shaft through the lumen into the sheath hub until the dilator hub engages the dilator centering device. The method includes disengaging the dilator hub from the dilator centering device with the dilator centering device staying attached to the sheath hub, and removing the dilator shaft from the sheath hub.

These and other features, aspects, and advantages of the apparatus and methods of the present technology will become better understood with regard to the following description and accompanying drawings. It is important to note this technology may be used for industrial purposes as well and that the descriptive use of the terms patient and vessels are for convenience only.

BRIEF DESCRIPTION OF THE DRAWINGS

In the drawings:

FIG. 33 is a perspective view of a dilator centering device with a revolved profile of less than 360 degrees.

DETAILED DESCRIPTION OF THE TECHNOLOGY

The present technology is directed to a dilator centering device and assemblies and methods using same. In particular, a dilator centering device in accordance with the disclosed technology can be used with a sheath hub assembly. In one embodiment, a dilator centering device includes a lumen capable of receiving a dilator shaft and substantially centering a dilator shaft with respect to the sheath hub as the dilator shaft enters the sheath hub. In one embodiment, the dilator centering device can be attached to the sheath hub during manufacturing or it can be attached at the use site. In one embodiment, the dilator centering device can be integrated with and non-removable from the sheath hub. The embodiments disclosed herein are illustrative and do not limit the scope and spirit of the disclosed technology.

Figure 1:
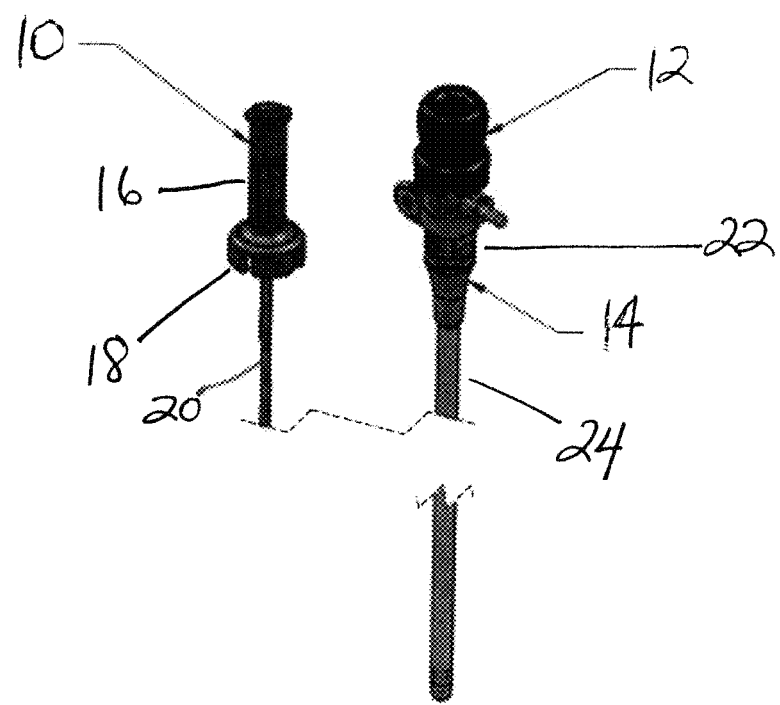
FIG. 1 is a diagram of an assembly having a dilator, a dilator centering device, and a sheath assembly, in accordance with one embodiment of the disclosed technology.

Referring now to FIG. 1, there is shown one embodiment of the disclosed dilator centering device and assembly. The illustrated embodiment shows a dilator 10, a dilator centering device 12, and a sheath assembly 14. The dilator 10 can include a handle portion 16, a hub portion 18, and a shaft portion 20. The sheath assembly 14 can include a hub portion 22 and a sheath portion 24.

The dilator centering device 12 disclosed herein has not heretofore been known in connection with dilators and sheath assemblies. Haemostatic valves in current sheath assemblies are generally made of rubber. These parts are prone to tearing from the tip of a dilator during insertion. Valve tears can lead to blood leakage during the interventional procedures, which can be problematic during medical procedures. Addressing this issue using different valve designs has been unsuccessful, as rubber valves are susceptible to tearing by dilators in this way. In addition, proper centering of the dilator tip during insertion may also be important, since it may reduce the likelihood of the dilator tip being damaged. A damaged dilator tip will prevent the smooth placement of the dilator/sheath assembly over the guide wire during a procedure.

The disclosed technology uses a dilator centering device. In one embodiment, the dilator and sheath assembly can be any such device previously or currently sold or used in the medical or industrial fields, and the disclosed dilator centering device can be configured to interoperate with previous or current dilators and sheath assemblies. Indeed, the disclosed dilator centering device can be configured to interoperate with future dilators or sheath assemblies not currently available in these fields. In one embodiment, rather than having a dilator centering device interoperate with previous or current dilators and sheath assemblies, each of a dilator, a sheath assembly, and a dilator centering device, can be configured in accordance with the disclosed technology.

Referring again to FIG. 1, the dilator centering device 12 is shown to be attached to the sheath assembly 14. In one embodiment, the dilator centering device 12 can be removably engaged with the sheath assembly 14, such that the dilator centering device 12 fits snugly with the sheath assembly 14 when attached, but is also detachable from the sheath assembly 14. In this embodiment, the dilator centering device 12 can be attached to the sheath assembly 14 during manufacturing or it can be attached at the use site or other site. In one embodiment, the dilator centering device 12 can be non-removably engaged with the sheath assembly 14, such that the dilator centering device 12 cannot be removed or is not designed to be removed or easily removed from the sheath assembly 14. In this embodiment, the dilator centering device 12 can be attached to the sheath assembly 14 during manufacturing or can be manufactured as an integrated instrument. In one embodiment, the dilator centering device 12 (either releasable or non-removable) can engage the sheath hub portion 22 of a sheath assembly 14.

Figure 2:
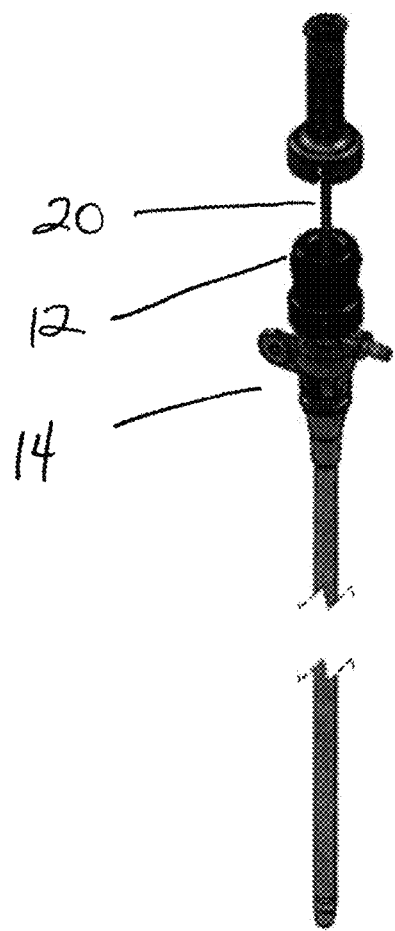
FIG. 2 is a diagram of the assembly of FIG. 1 showing the dilator partially inserted into the dilator centering device and the sheath assembly.

Referring now to FIG. 2, there is shown a diagram of the device and assembly of FIG. 1, with the dilator shaft 20 partially inserted into the dilator centering device 12 and the sheath assembly 14. The dilator centering device 12 includes a lumen (not shown) capable of receiving the dilator shaft 20 and substantially centering a dilator shaft 20 with respect to the sheath hub 22 as the dilator shaft 20 enters the sheath hub 22. Various lumen designs in accordance with the disclosed technology are described below herein with respect to FIGS. 5-23.

Figure 3:
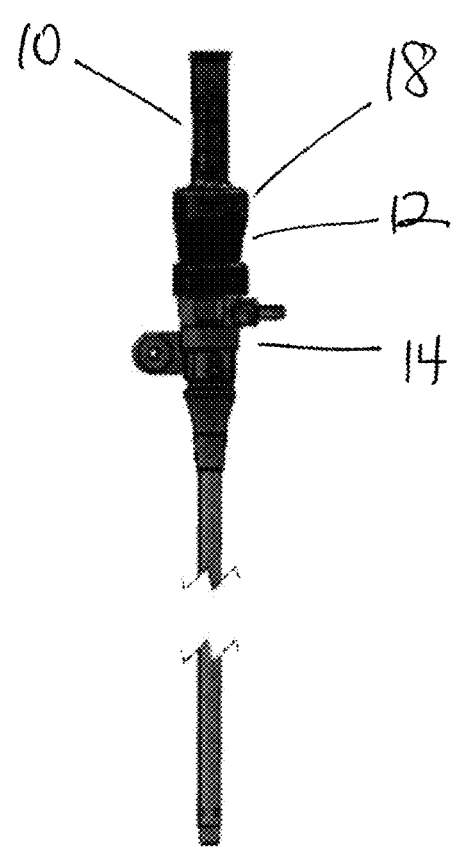
FIG. 3 is a diagram of the assembly of FIG. 1 showing the dilator fully engaged with the dilator centering device.

Referring now to FIG. 3, there is shown a diagram of the device and assembly of FIGS. 1 and 2, with the dilator shaft fully inserted into the dilator centering device 12 and the sheath assembly 14. In the illustration, the dilator 10 is fully engaged with the dilator centering device 12. As illustrated, the hub portion 18 of the dilator 10 can attach to the proximal side of the dilator centering device 12. In one embodiment, the dilator 10 can removably attach to the dilator centering device 12, e.g., the proximal side of the dilator centering device. In one embodiment, the dilator 10 can non-removably attach to the dilator centering device 12, e.g., the proximal side of the dilator centering device. In this state, the fully engaged dilator/sheath assembly is operable for vascular access to a patient's body.

In one embodiment (not shown), after the assembly is in the state shown in FIG. 3, an additional step may be required based on a particular embodiment of the dilator centering device. Specifically, in one embodiment, the dilator centering device can be configured to come apart when a threshold force is applied to its proximal and distal ends, e.g., by forcing the dilator against the dilator centering device. In this embodiment, application of the threshold force can cause the dilator centering device to come apart and completely disengage from the dilator and the sheath assembly. Then, the dilator can be directly attached to the sheath assembly.

After the dilator/sheath assembly is in the artery, the dilator can be removed from the sheath. Three separate embodiments of the disclosed technology will now be described for removal of the dilator. The embodiments are merely illustrative and do not limit the spirit and scope of the disclosed technology.

Figure 4:
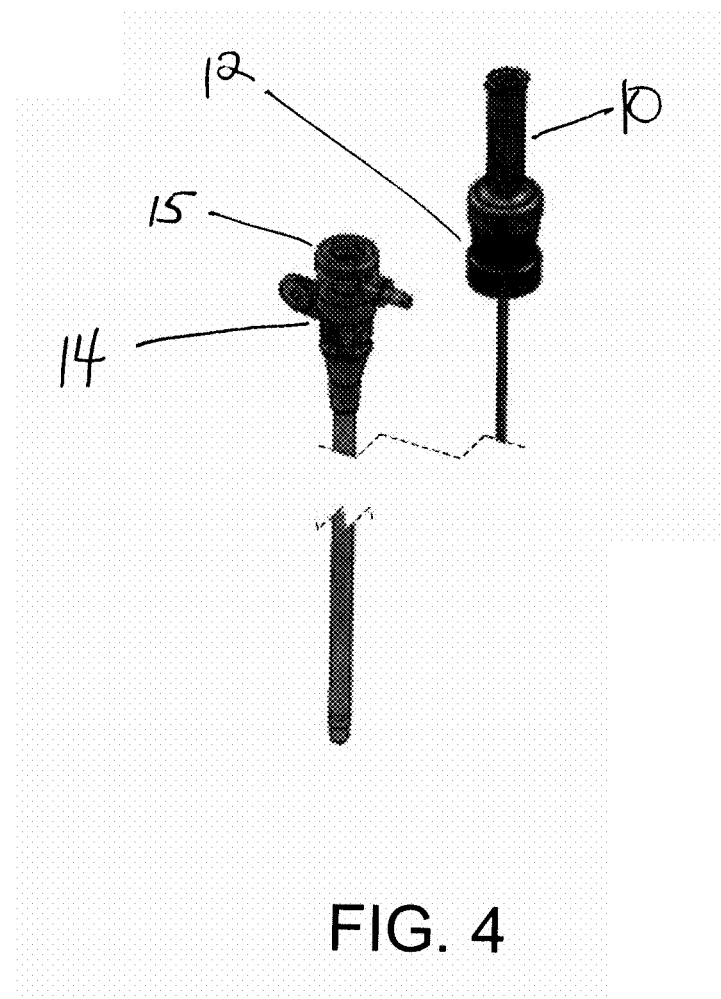
FIG. 4 is a diagram of one embodiment of a dilator, dilator centering device, and sheath assembly.

In one embodiment, with reference to FIG. 4, the dilator centering device 12 can be removably attached to the sheath assembly 14, such that the dilator centering device 12 can be detached from the sheath assembly 14. At the same time, the dilator center device 12 can be engaged with the dilator 10 (either removably or non-removably). Here, a dilator 10 remains locked to the centering device 12 after removal from sheath. If the dilator centering device 12 is non-removably attached to the dilator 10, then removal of the dilator 10 will also disengage the dilator centering device 12 from the sheath assembly 14. If the dilator centering device 12 is removably attached to the dilator 10, then in one embodiment the dilator 10 can be detached from the dilator centering device 12, and then the dilator center device 12 can be detached from the sheath assembly (not shown). In one embodiment, even if the dilator centering device is removably attached to the dilator, the attachment between the dilator and the dilator centering device can be stronger than the attachment between the dilator centering device and the sheath assembly, such that removal of the dilator will disengage the dilator centering device from the sheath assembly.

In the second embodiment, with reference now to FIG. 2, the dilator centering device 12 can be non-removably attached to the sheath assembly 14. In this embodiment, removal of the dilator does not detach the dilator centering device from the sheath assembly.

In the third embodiment (not shown), a previously described embodiment of the dilator centering device allowed the device to come apart so that the dilator can be directly attached to the sheath assembly. In such embodiment, the dilator can be removed from the sheath by disengaging the dilator from the sheath assembly.

What has been described thus far are various embodiments of a dilator, dilator centering device, and sheath assembly, in accordance with the disclosed technology, and different operation of the assembly depending on the various embodiments. The embodiments are merely illustrative and do not limit the spirit or scope of the disclosed technology. For example, different embodiments disclosed herein may be combined in multiple different ways to provide other assemblies not specifically illustrated herein.

The detailed description below will now describe various embodiments of the dilator centering device. As described above, a dilator centering device in accordance with one embodiment of the disclosed technology can be attached to the sheath assembly during manufacturing or it can be attached at the use site or other site. In one embodiment, the dilator centering device can be integrated with and non-removable from the sheath hub. Also, in one embodiment, the disclosed dilator centering device can be configured to interoperate with previous, current, or future dilators or sheath assemblies. In one embodiment, rather than having a dilator centering device interoperate with previous or current dilators and sheath assemblies, each of a dilator, a sheath assembly, and a dilator centering device, can be configured in accordance with the disclosed technology.

In one embodiment, a dilator centering device can be composed of plastic and can be manufactured by injection molding. Those skilled in the art will recognize that other materials and manufacturing methods can be used.

Figure 5:
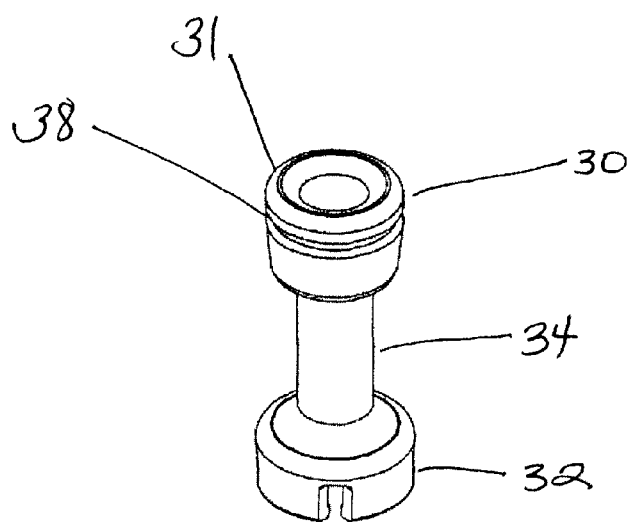
FIG. 5 is a perspective view of a dilator centering device in accordance with one embodiment of the disclosed technology.
Figure 6:
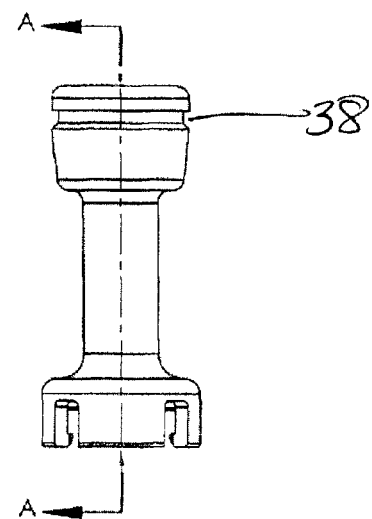
FIG. 6 is a side view of the dilator centering device of FIG. 5.
Figure 7:
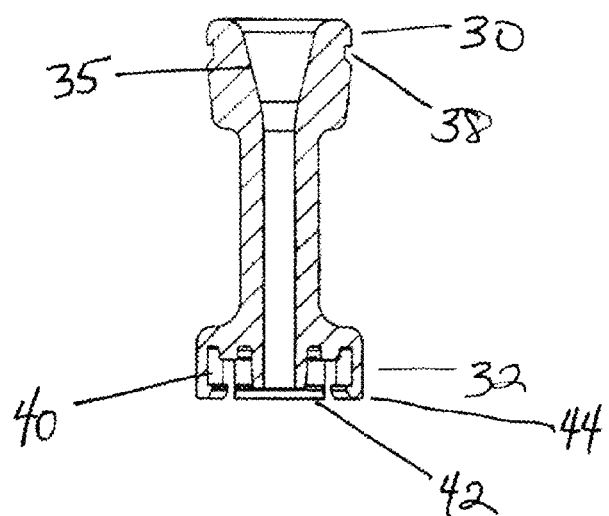
FIG. 7 is a cross-sectional view of the dilator centering device of FIG. 5.

FIGS. 5-7 show different perspectives of one embodiment of a dilator centering device 30. FIG. 5 shows a perspective view, FIG. 6 shows a side view, and FIG. 7 shows a cross-sectional view of the dilator centering device embodiment. The illustrated embodiment includes a proximal structure 31 having an opening, a distal structure 32 also having an opening, and a center structure 34 having a lumen that connects the proximal and distal openings. In operation, the proximal and distal openings and the lumen receive a dilator shaft. The lumen is configured so that it can substantially center the dilator shaft with respect to the sheath assembly when the dilator shaft enters the sheath assembly. As shown in FIG. 7, in one embodiment, the lumen can be more narrow than the proximal opening to allow easier insertion of the dilator shaft into the proximal opening, and to substantially center the dilator shaft as it enters and passes through the lumen. In one embodiment, a dilator centering device can be in the range from one-half to about five centimeters from the proximal end to the distal end. In one embodiment, the lumen can be in the range from one to about eight millimeters. FIG. 7 also shows a tapered section 35 that joins the proximal opening and lumen.

In one aspect of the disclosed technology, and with continuing reference to FIGS. 5-7, the proximal structure in the dilator centering device 30 can include a locking mechanism 38 for engaging a dilator. In one embodiment, the locking mechanism 38 can engage a hub portion of a dilator. In the illustrated embodiment, the locking mechanism 38 of the proximal structure is a circumferential groove on the outside surface of the proximal structure. As disclosed above, in various embodiments, the locking mechanism can removably or non-removably engage a dilator. One skilled in the art will recognize that a circumferential groove is merely illustrative, and other types of locking mechanisms can be used with the proximal structure for engaging a dilator.

In one aspect of the disclosed technology, and with continuing reference to FIGS. 5-7, the distal structure in the dilator centering device can include a locking mechanism 40 for engaging a sheath assembly. In one embodiment, the locking mechanism 40 can engage a hub portion of a sheath assembly. In the illustrated embodiment, the locking mechanism 40 of the distal structure includes an inner stem 42 and flanges 44 surrounding the inner stem. The inner stem 42 is configured to fit into the sheath hub, and the flanges 44 are configured to engage the outer surface of the sheath hub. As disclosed above, in various embodiments, the locking mechanism 40 of the distal structure can removably or non-removably engage a sheath assembly. In one embodiment, the dilator centering device 30 can be non-removably integrated with the sheath assembly during manufacturing. One skilled in the art will recognize that an inner stem and flanges are merely illustrative, and other types of locking mechanisms can be used with the proximal structure for engaging a dilator. For example, a distal structure locking mechanism need not have multiple flanges, and rather, can have a single circumferential flange.

As described above, in one embodiment, the dilator centering device can be configured to come apart when a threshold force is applied to its proximal end, or to both the proximal and distal ends. For example, when the distal end of the dilator centering device is engaged with a sheath assembly and the proximal end is engaged with a dilator, a force applied from the dilator to the dilator centering device can cause the dilator centering device to come apart into two pieces or more than two pieces.

What has been described above are various portions of a dilator centering device. In one aspect of the disclosed technology, a dilator centering device can include a seal within the lumen. A seal can operate to slow the movement of a dilator shaft as it progresses through the lumen and into a sheath hub and sheath. This slower movement of a dilator can reduce the contact force between a dilator shaft and any valves in the sheath hub and mitigate impact to such valves. A seal can be made of various materials known in the art.

Figure 20:
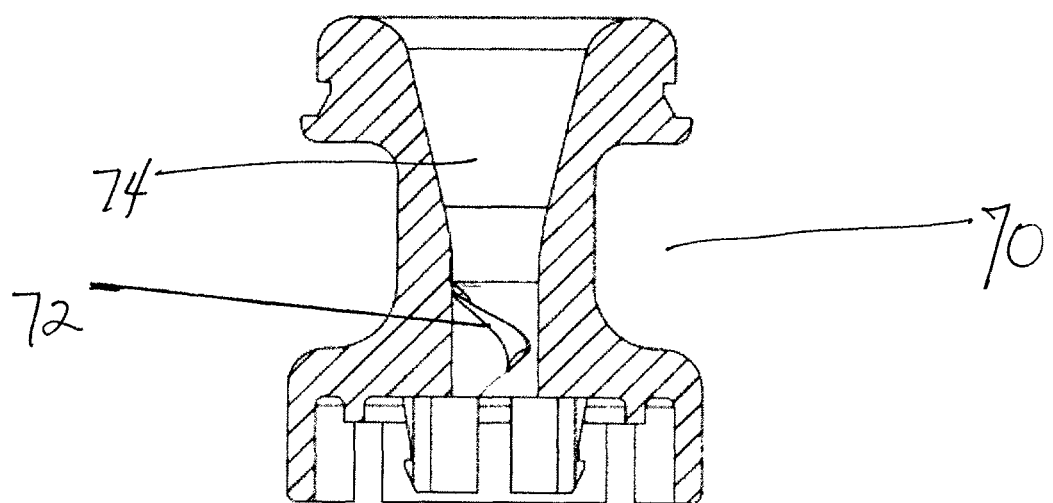
FIG. 20 is a cross-sectional view of the dilator centering device of FIG. 17.
Figure 21:
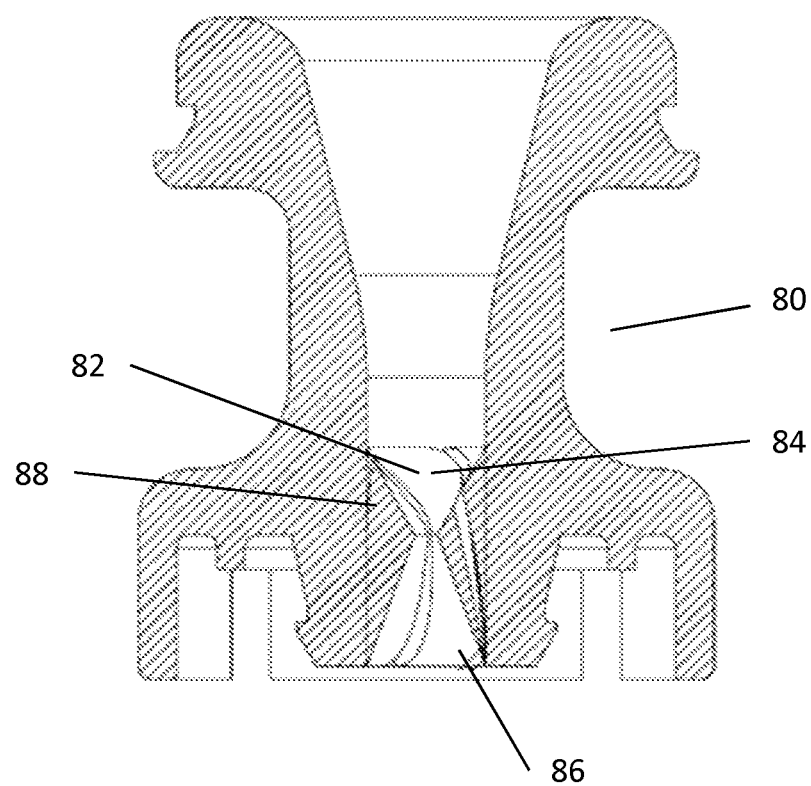
FIG. 21 is a cross-sectional view of a dilator centering device with a spiral double-funnel seal in accordance with one aspect of the disclosed technology.
Figure 22:
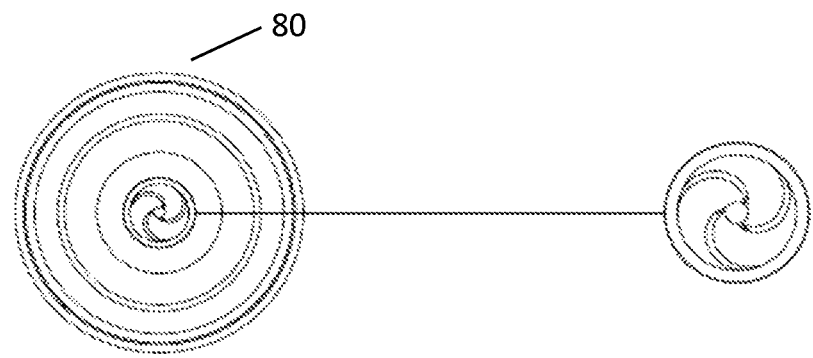
FIG. 22 is a top view of the dilator centering device of FIG. 21.
Figure 23:
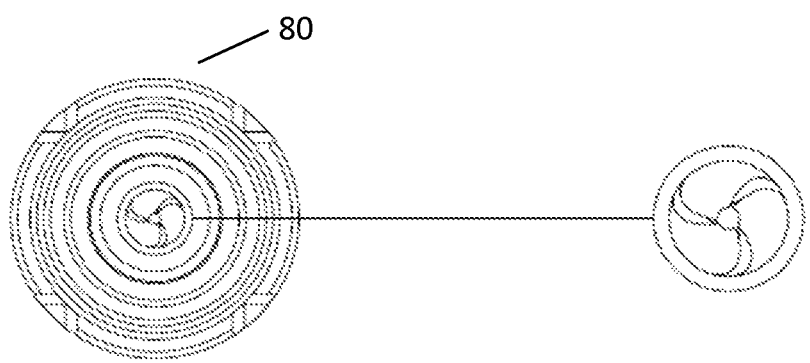
FIG. 23 is a bottom view of the dilator centering device of FIG. 21.

The following detailed description will now describe various embodiments for a seal within a lumen of a dilator centering device. FIGS. 8-16 illustrate an embodiment of a funnel seal, FIGS. 17-20 illustrate an embodiment of a spiral funnel seal, and FIGS. 21-23 illustrate an embodiment of a spiral double-funnel seal in accordance with the disclosed technology. The figures and embodiments are merely illustrative and do not limit the scope and spirit of the disclosed technology. One skilled in the art will recognize that a seal can have other shapes, configurations, orientations, and aspects not specifically illustrated herein.

Figure 8:
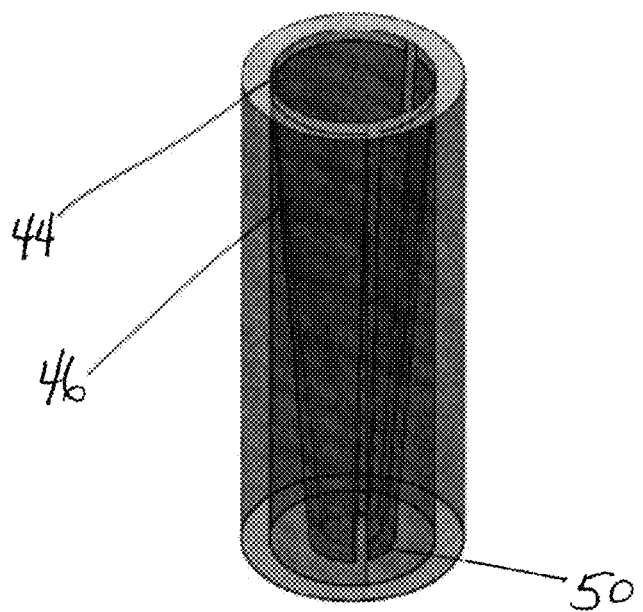
FIG. 8 is a perspective view of a funnel seal and lumen in accordance with one embodiment of the disclosed technology.

Referring now to FIG. 8, there is shown a perspective view of a funnel seal and lumen in accordance with one embodiment of the disclosed technology. The illustrated embodiment includes a lumen wall 44 and a three-flap funnel seal 46. The illustrated lumen may be the entire lumen within a dilator centering device, or a portion of the entire lumen. The seal can be secured to the lumen wall 44 at the proximal end of the seal, and can be free-moving at the distal end of the seal 50. As illustrated, there can gradually be greater distance between the lumen wall and the seal when advancing from the proximal end to the distal end of the seal. As a dilator shaft progresses through the lumen, it will reach gradually narrower portions of the funnel seal and its progress will be slowed by the funnel seal.

Figure 9:
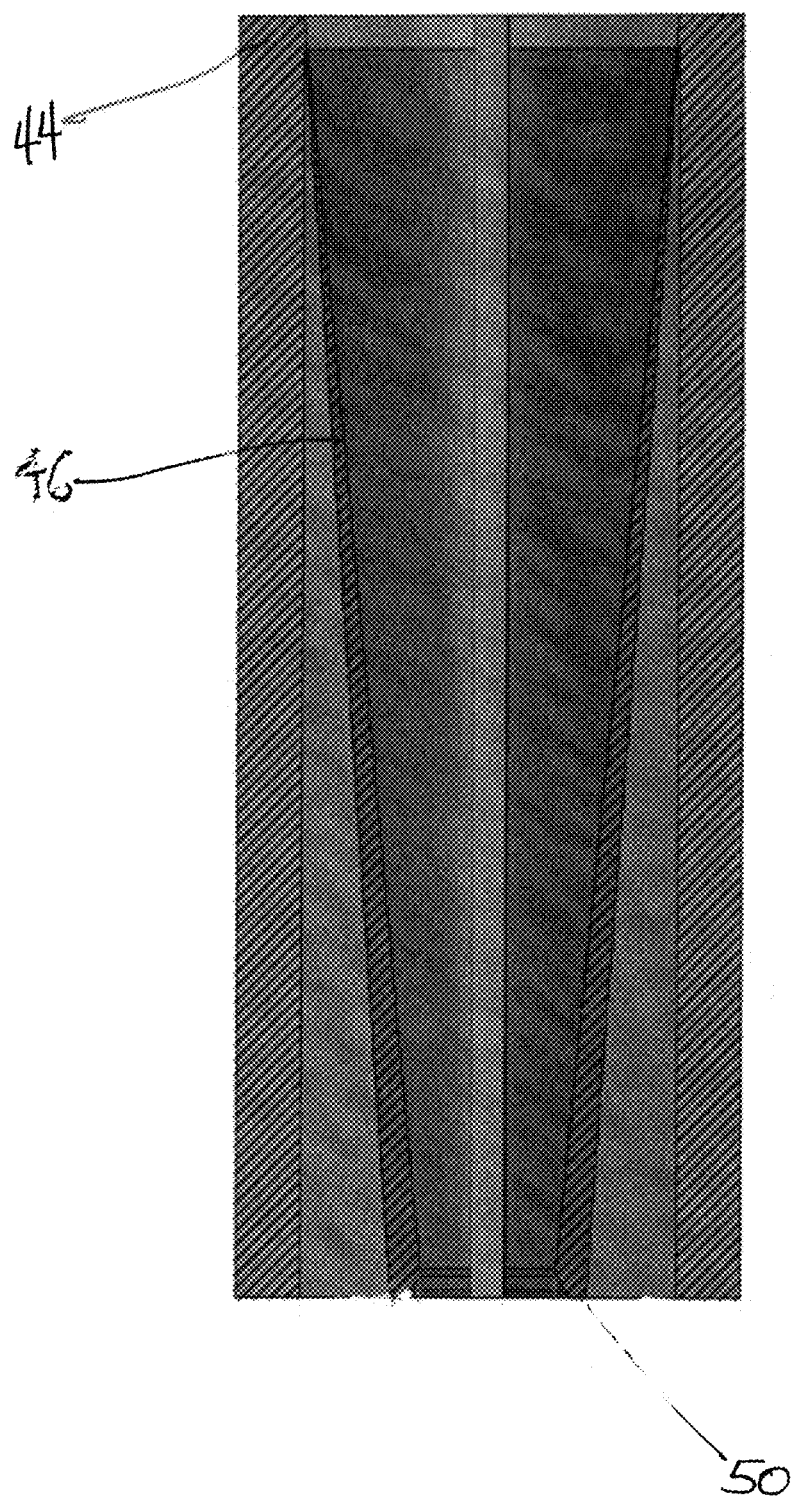
FIG. 9 is a cross-sectional view of the funnel seal and lumen of FIG. 8.
Figure 10:
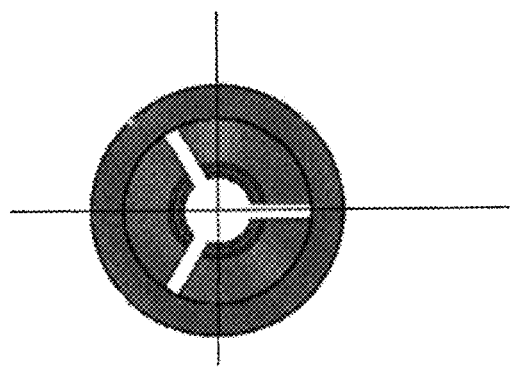
FIG. 10 is a top view of the funnel seal and lumen of FIG. 8.
Figure 11:
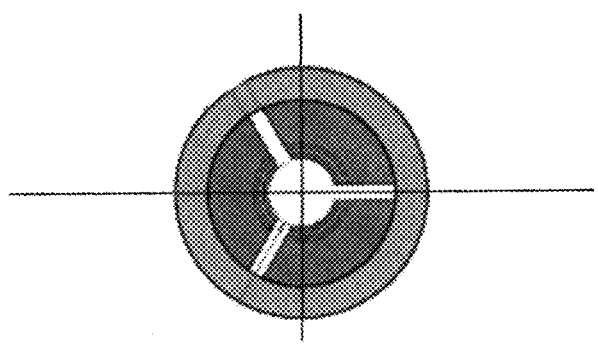
FIG. 11 is a bottom view of the funnel seal and lumen of FIG. 8.
Figure 12:
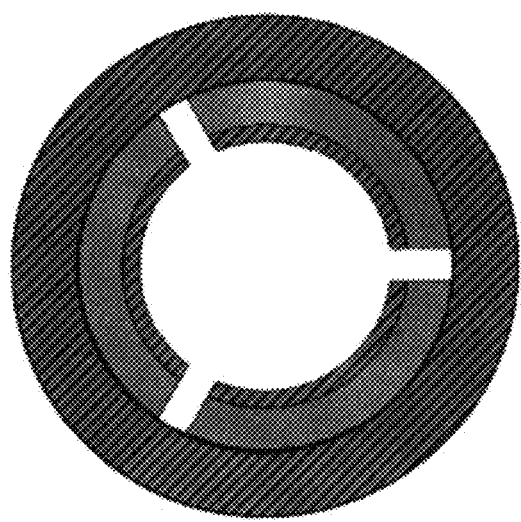
FIG. 12 is a cross-sectional view of the funnel seal and lumen of FIG. 8.

FIG. 9 shows a cross-sectional view of the funnel seal and lumen of FIG. 8, with the lumen and seal sliced lengthwise to form two half-pipes. Like elements are labeled with the same numerals as those in FIG. 8. FIGS. 10 and 11 area top and bottom views, respectively, of the funnel seal and lumen of FIG. 8. FIG. 12 is a cross-sectional view of the funnel seal and lumen of FIG. 8, with the lumen and seal sliced cross-wise between the ends of the lumen, at the proximal end of the seal.

Figure 13:
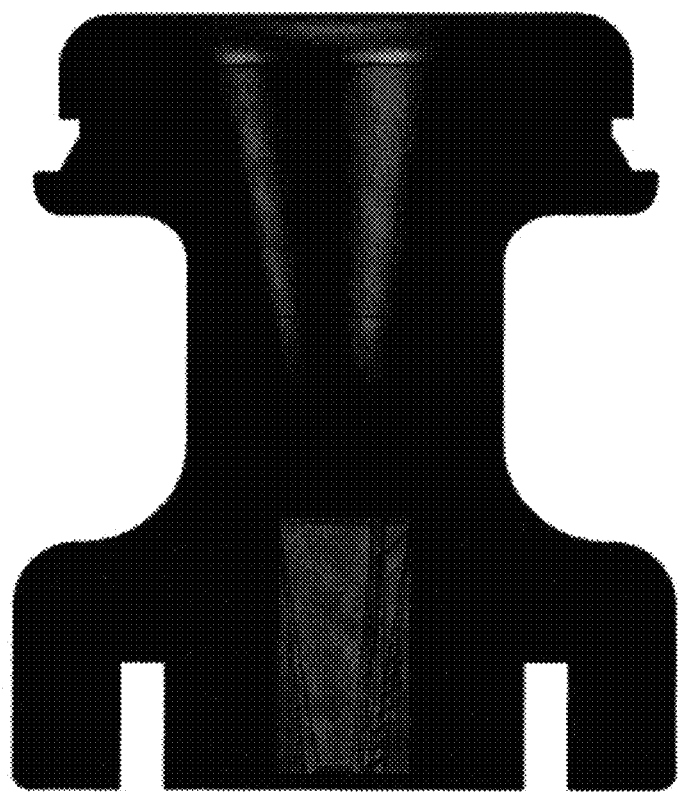
FIG. 13 is a cross-sectional view of a dilator centering device with a funnel seal in accordance with one embodiment of the disclosed technology.

FIG. 13 shows a cross-sectional view of a dilator centering device having a funnel seal within a portion of the lumen. As shown in FIG. 13, a seal need not span the entire length of a lumen. In other embodiments (not shown), however, a seal can span the entire length of a lumen, and in some embodiments can protrude beyond a lumen and through the distal opening.

Figure 14:
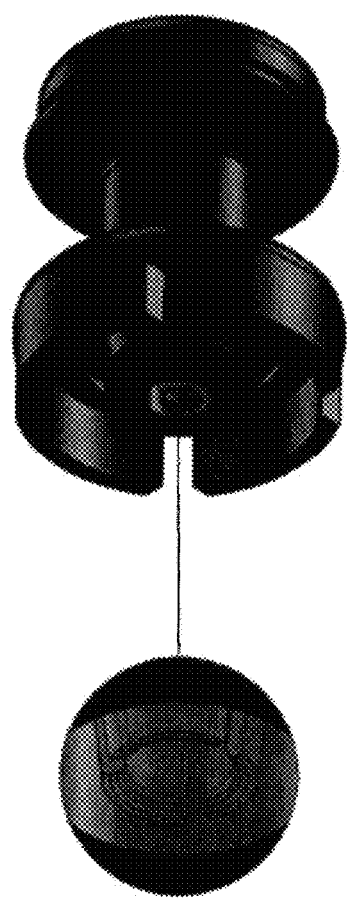
FIG. 14 is a perspective view of the dilator centering device of FIG. 13.
Figure 15:
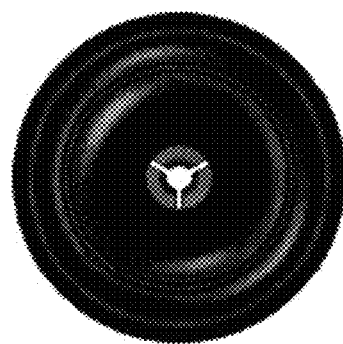
FIG. 15 is a top view of the dilator centering device of FIG. 13.
Figure 15:
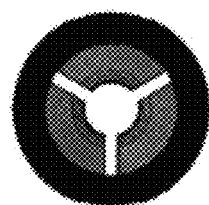
Figure 16:
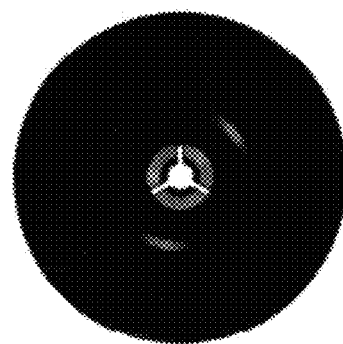
FIG. 16 is a bottom view of the dilator centering device of FIG. 13.
Figure 16:
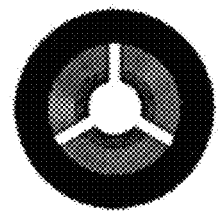

FIG. 14 is a perspective view of the dilator centering device having a funnel seal. FIGS. 15 and 16 are top and bottom views, respectively, of the dilator centering device and lumen having a funnel seal. The illustrated embodiment is merely exemplary and does not limit the scope and spirit of the disclosed technology.

Figure 17:
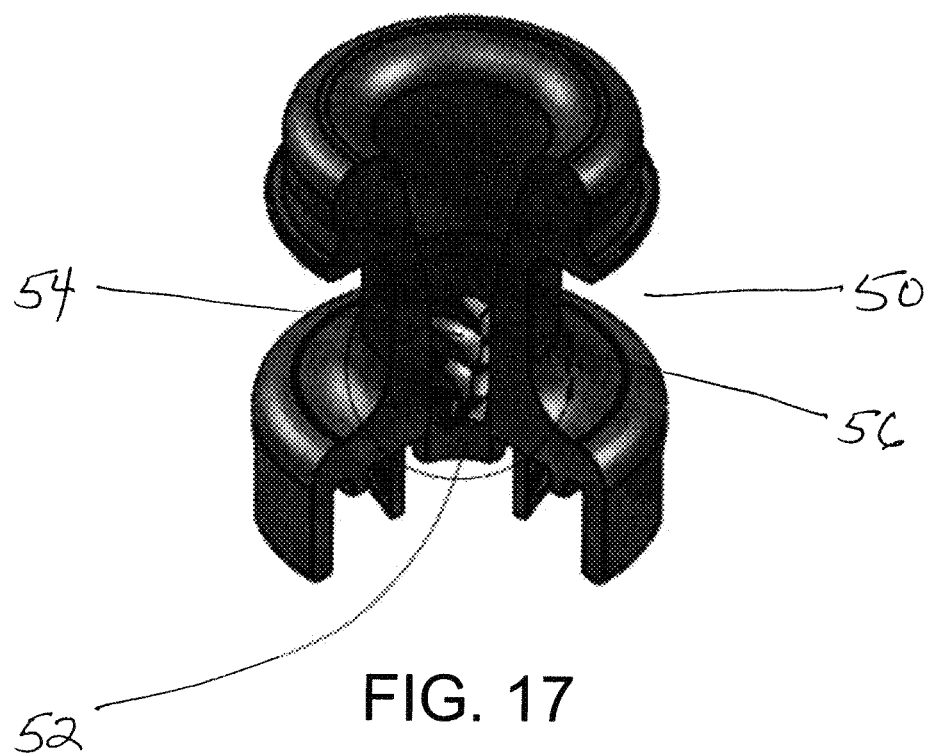
FIG. 17 is a perspective view of a dilator centering device with a spiral funnel seal in accordance with one embodiment of the disclosed technology.
Figure 18:
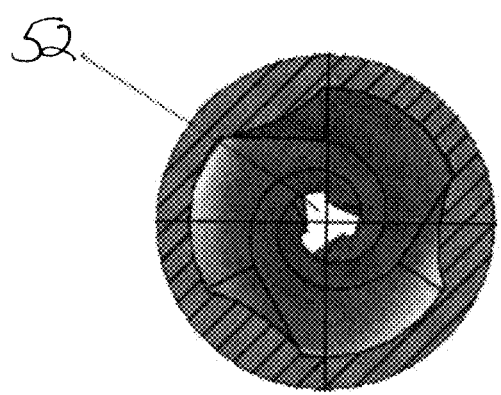
FIG. 18 is top view of the lumen and spiral funnel seal of FIG. 17.

Referring now to FIG. 17, there is shown a perspective view of a dilator centering device with a spiral funnel seal 50 in accordance with one embodiment of the disclosed technology. A portion of the dilator centering device is removed to reveal a view of the inner portions of the dilator centering device. FIG. 18 is a top view of the lumen 52 and spiral funnel seal of FIG. 17. In the illustrated embodiment, three flaps 54 form the spiral funnel seal. The flaps 54 can be secured to the lumen wall 56 at the proximal end of the seal and free-moving at the distal end of the seal. The spiral funnel seal can gradually become narrower from the proximal end to the distal end of the seal. That is, the distance between the lumen wall 56 and the spiral funnel seal 50 can gradually become greater from the proximal end to the distal end of the seal. Due to its configuration, a spiral funnel seal can provide greater capability to slow the progress of a dilator shaft through the seal, compared to a funnel seal.

Figure 19:
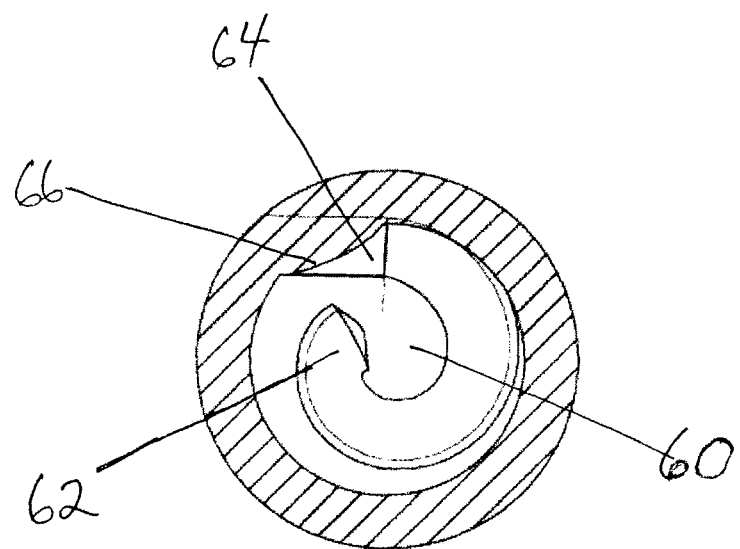
FIG. 19 is a top view of the lumen and one flap of the spiral funnel seal of FIG. 17.

FIG. 19 is a schematic top view of a lumen 60 and one flap 62 of a spiral funnel seal. As shown in FIG. 19, the proximal end 64 of the flap can be secured to the lumen wall 66, and the distal end of the flap can be free moving. FIG. 20 is a cross-sectional view of a dilator centering device 70 having a spiral funnel seal 72 in the lumen 74. The illustrated embodiment is merely exemplary and does not limit the scope and spirit of the disclosed technology.

Referring now to FIG. 21, there is shown a cross-sectional view of a dilator centering device 80 with a spiral double-funnel seal 82 in accordance with one embodiment of the disclosed technology. In the illustrated embodiment, the spiral double-funnel has an "hourglass" type configuration with the narrowest portion of the seal located in between the proximal 84 and distal 86 ends of the seal. In the illustrated embodiment, the spiral double-funnel 82 can be secured to the lumen wall 88 at both the proximal 84 and distal 86 ends of the seal. This configuration can provide the capability to slow the progress of a dilator shaft through the lumen and sheath hub during both insertion and removal of the dilator shaft because both the proximal 84 and distal 86 ends of the seal are secured to the lumen wall 88. With the spiral double-funnel seal 82, potential impact to any valves in a sheath hub can be mitigated during dilator removal. FIGS. 22 and 23 are top and bottom views of the dilator centering device 80 and lumen having a spiral double-funnel seal. The illustrated embodiment is merely exemplary and does not limit the scope and spirit of the disclosed technology.

Figure 24:
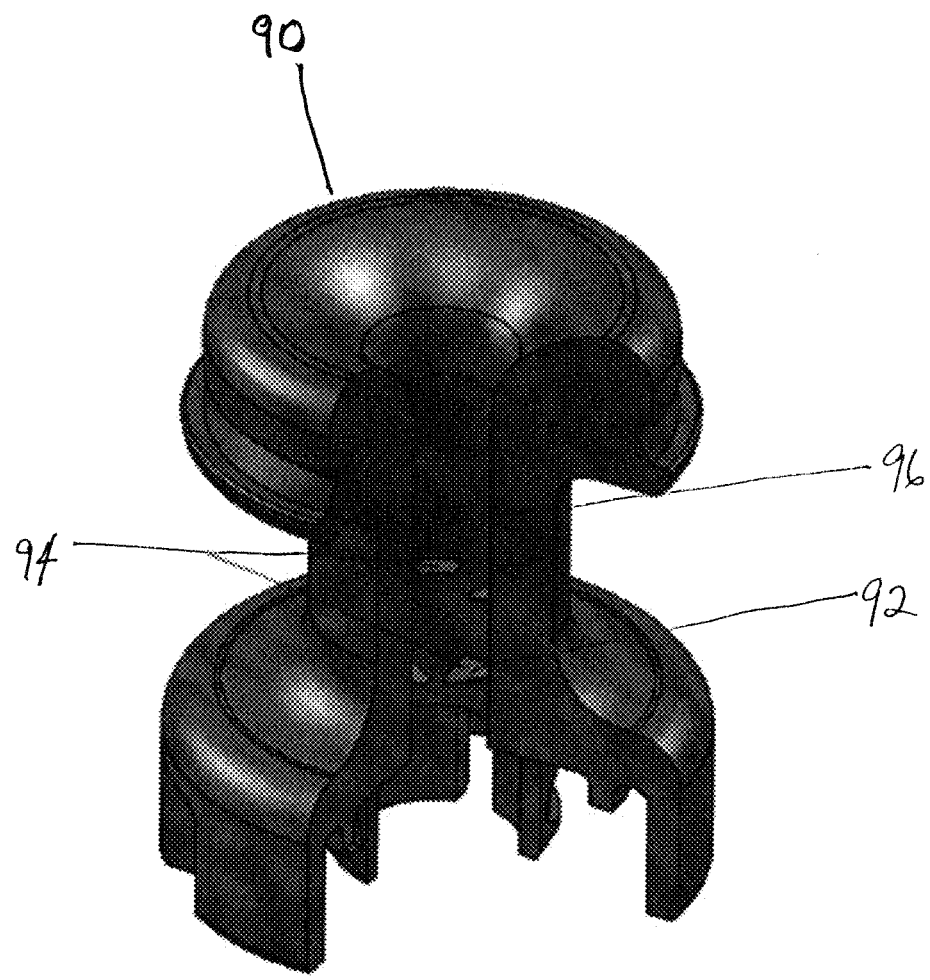
FIG. 24 is a perspective view of a dilator centering device with a multiple hinged flap seal in accordance with one embodiment of the disclosed technology.
Figure 25:
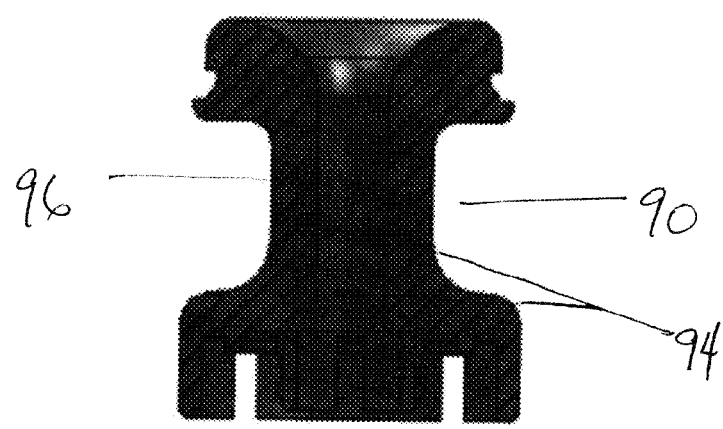
FIG. 25 is a cross-sectional view of the dilator centering device of FIG. 24.
Figure 26:
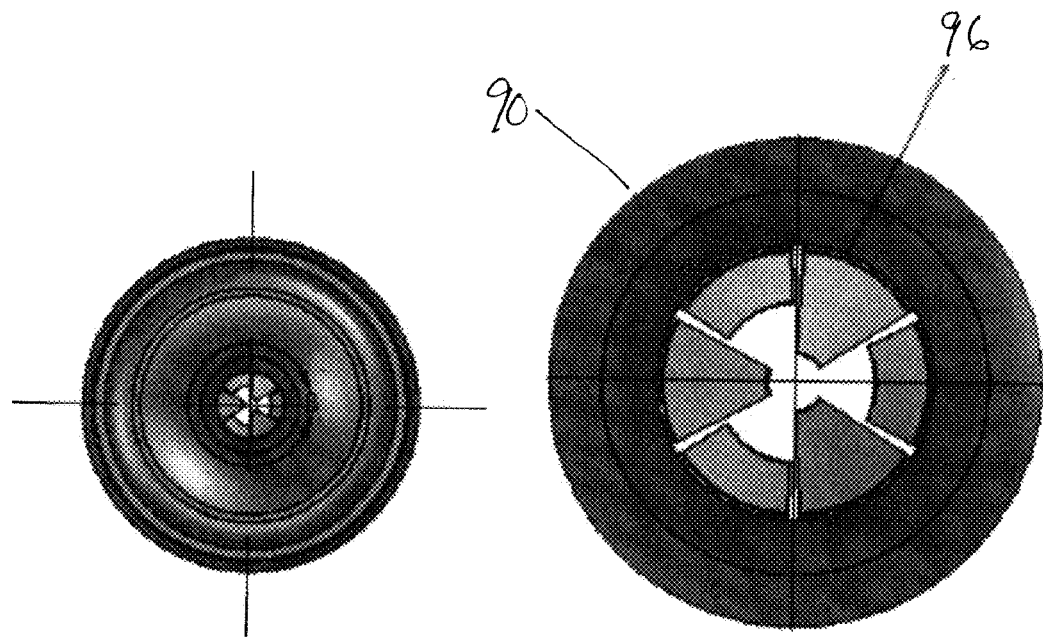
FIG. 26 is a top view of the dilator centering device and lumen of FIG. 24.

Referring now to FIG. 24, there is shown a perspective view of a dilator centering device 90 with a multiple hinged flap seal 92 in accordance with one embodiment of the disclosed technology. As shown in the illustration, the seal 92 includes multiple, smaller flaps 94 that are each "hinged" to the inner wall 96 of the lumen. The flaps 94 may not be "hinged" in the mechanical sense, but rather the flaps 94 are each secured to the lumen wall 96 in a way that allows each flap to bend towards the distal end or the proximal end of the lumen. In this configuration, the multiple hinged flap seal 92 is capable of slowing the progression of dilator shaft during insertion and removal of the dilator through the sheath hub. Because the smaller flaps 94 have less surface area than the funnel seal, spiral funnel seal, or spiral double-funnel seal, a dilator shaft may progress through the seal of FIG. 24 faster than with the aforementioned seals. This configuration, however, can be more cost-effective and can still provide effective slowing and substantially centering of a dilator shaft. FIG. 25 is a cross-sectional view of the dilator centering device with a multiple hinged flap seal, and FIG. 26 is a top view of same. The illustrated embodiment is merely exemplary and does not limit the scope and spirit of the disclosed technology.

Figure 27:
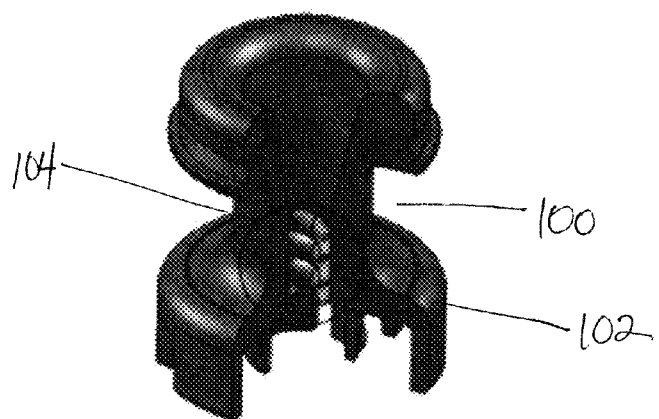
FIG. 27 is a perspective view of a dilator centering device with a multiple hinged spiral flap seal in accordance with one embodiment of the disclosed technology.
Figure 28:
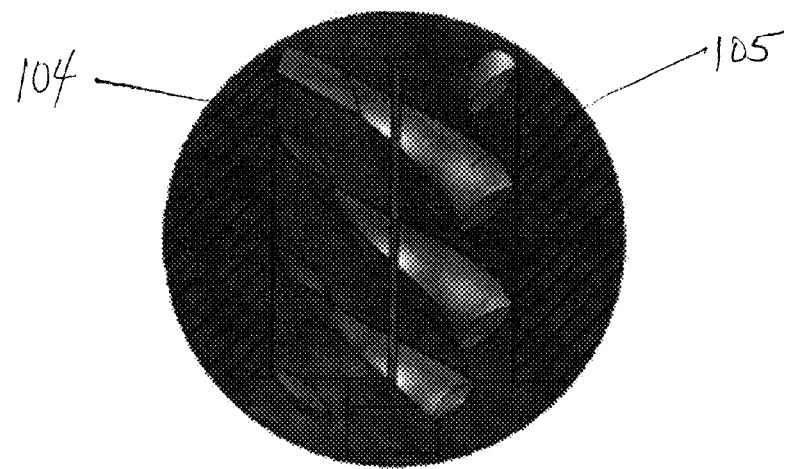
FIG. 28 is cross-sectional view of the seal and lumen of FIG. 27.

Referring now to FIG. 27, there is shown a perspective view of a dilator centering device 100 with a multiple hinged spiral flap seal 102 in accordance with one embodiment of the disclosed technology. FIG. 28 is an enlargement of the lumen and seal portion of the dilator centering device. As shown in the illustration, the seal includes multiple flaps 105 that are each in the shape of a spiral segment and are "hinged" to the inner wall 104 of the lumen. Because the spiral segment flaps 105 are larger than the flaps in FIG. 24, these flaps can provide a greater ability to slow the progress of the dilator shaft through the lumen and sheath hub than the multiple hinged flap seal. But at the same time, they may have higher production cost.

Figure 29:
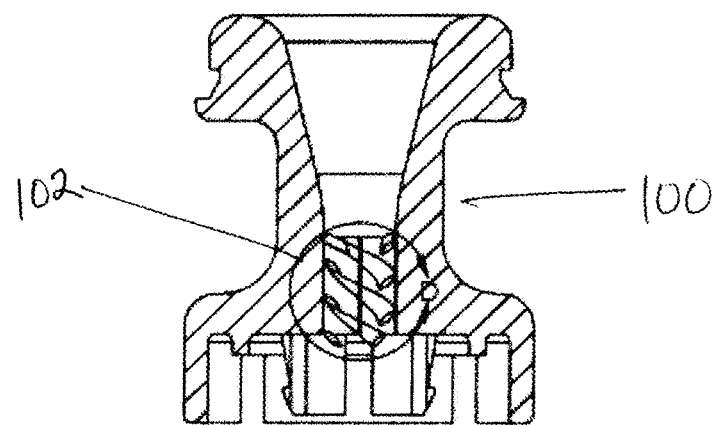
FIG. 29 is a cross-sectional view of the dilator centering device of FIG. 27.
Figure 30:
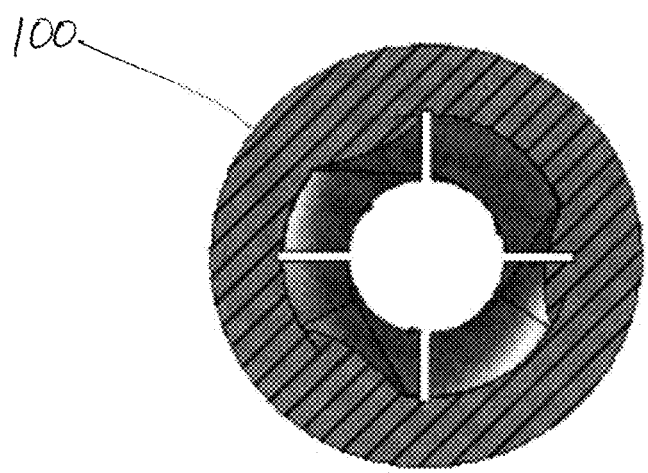
FIG. 30 is a top view of the seal and lumen of FIG. 27.

FIG. 29 is a cross-sectional view of the dilator centering device 100 with a multiple hinged spiral flap seal 102, and FIG. 26 is a top view of same. The illustrated embodiment is merely exemplary and does not limit the scope and spirit of the disclosed technology.

Figure 31:
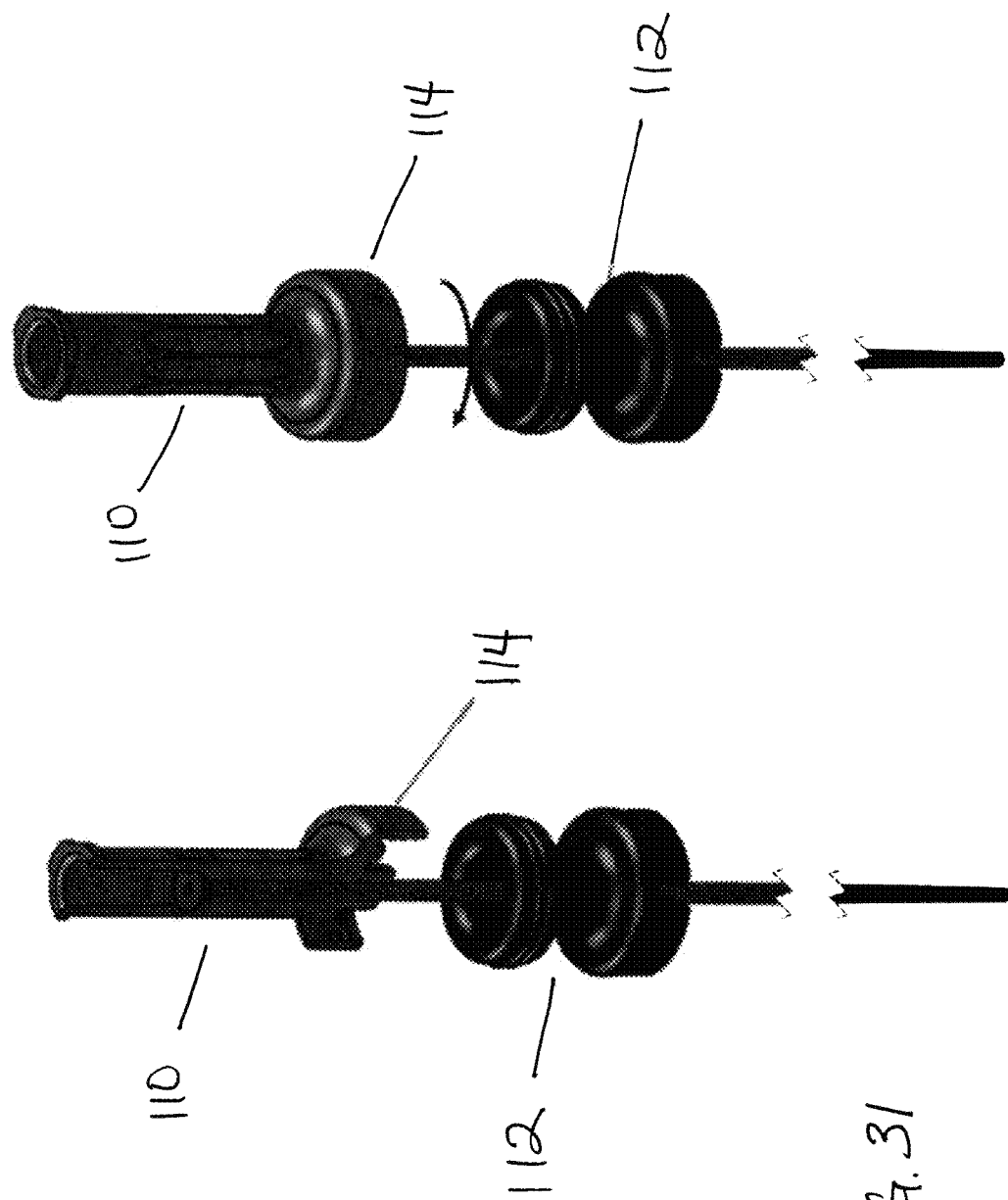
FIG. 31 is a perspective view and cross sectional view of a dilator and dilator centering device with threaded connection.

FIG. 31 is an illustration of an embodiment of the technology comprising a threaded connection between a dilator 110 and a dilator centering device 112. The figure illustrates a screw or quarter turn locking interface and can be incorporated with either the interface between the dilator centering device 112 to the sheath hub (not shown), to the interface between dilator hub 114 and dilator centering device 112 or both.

Figure 32:
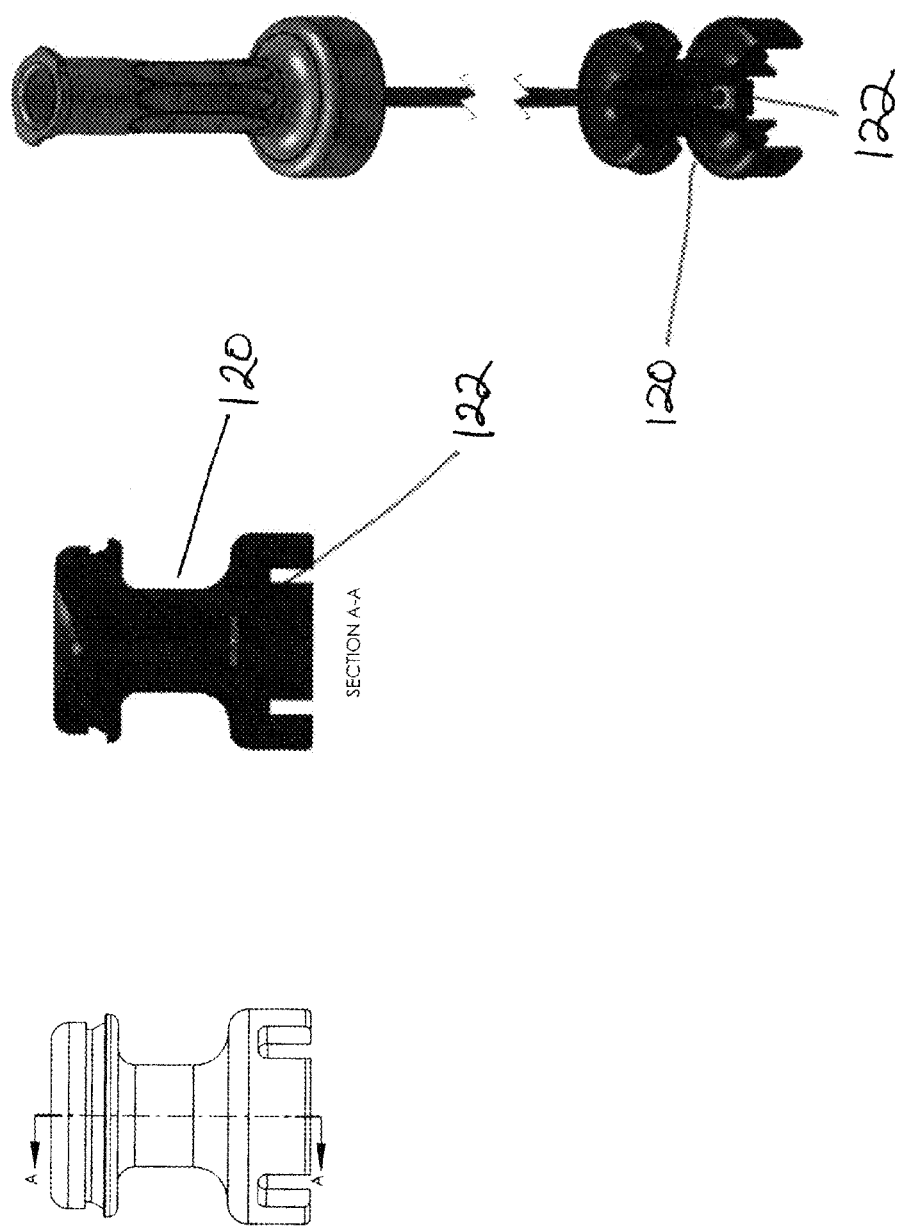
FIG. 32 is three views of a dilator and dilator centering device with a valve.

FIG. 32 is an illustration of an embodiment of the technology comprising a dilator centering device 120 with a valve 122, made out of silicon or other elastic material, which is positioned closer to the distal end of the centering device to help position the dilator tip, preferably in substantially the center of the dilator centering device.

FIG. 33 is an illustration of an embodiment of the technology comprising a dilator centering device 130 that is "C shaped" or having a revolved profile less than 360 degrees. This embodiment may be comprised of a revolved profile that is anywhere from 5 degrees to less than 360 degrees. In this embodiment the dilator centering device 130 comprises a channel formed by a channel wall 132 for receiving a dilator shaft.

Accordingly, what have been described are various embodiments of a dilator, dilator centering device, seal for a lumen of a dilator centering device, and sheath assembly, in accordance with the disclosed technology, and different ways to operate the various assemblies depending on the various embodiments. The embodiments are merely illustrative and do not limit the spirit or scope of the disclosed technology. For example, different embodiments disclosed herein may be combined in multiple different ways to provide other assemblies not specifically illustrated herein. All embodiments described herein are illustrative and in no way limit the scope of the technology, and the technology may be embodied in other forms not explicitly described here, without departing from the spirit thereof.

What is claimed is:

1. A device for use with a dilator, the device comprising:
   a proximal structure configured to engage a dilator, the proximal structure having a first opening capable of receiving a dilator shaft of the dilator;
   a distal structure configured to engage a sheath assembly comprising a sheath hub and a sheath, the distal structure having a second opening capable of receiving the dilator shaft; and
   a center structure between the proximal structure and the distal structure, wherein the proximal structure, the distal structure, and the center structure are integrated and form a continuous lumen interposed between the first opening and the second opening, wherein the lumen tapers from the first opening to the center structure and is capable of receiving the dilator shaft, wherein each of the proximal structure, the distal structure, and the center structure is separate from the dilator and from the sheath assembly, the sheath hub, and the sheath.

2. A device as in claim 1, wherein the distal structure is configured to engage the sheath assembly by a releasable locking mechanism.

3. A device as in claim 2, wherein the releasable locking mechanism comprises:
an inner stem surrounding the second opening and configured to fit into the sheath assembly; and
at least one flange around the inner stem configured to removably engage an outer surface of the sheath assembly.

4. A device as in claim 2, further comprising the sheath assembly engaged with the releasable locking mechanism of the distal structure.

5. A device as in claim 1, further comprising the sheath assembly non-removably engaged with the distal structure.

6. A device as in claim 1, wherein the proximal structure, the centering structure, and the distal structure are each configured to come apart when a threshold force is applied to at least the proximal structure.

7. A device as in claim 1, wherein the proximal structure is configured to engage the dilator by a locking mechanism configured to engage a dilator hub of the dilator.

8. A device as in claim 7, wherein the locking mechanism is a circumferential groove on an outer surface of the proximal structure.

9. A device as in claim 1, further comprising a seal within the lumen and spanning at least a portion of the lumen.

10. A device as in claim 9, wherein the seal is configured in at least one of: a funnel configuration, a spiral funnel configuration, a spiral double-funnel configuration, a multiple hinged flap configuration, and a multiple hinged spiral-flap configuration.

11. A device as in claim 9, wherein the seal is a funnel seal comprising at least three flaps.

12. A device as in claim 9, wherein the seal is a spiral double-funnel seal.

13. An apparatus, comprising:
a dilator comprising a dilator hub and a dilator shaft connected to the dilator hub;
a sheath assembly capable of receiving the dilator shaft, the sheath assembly comprising a sheath hub and a sheath; and
a dilator centering device engaged with the sheath assembly, the dilator centering device comprising a continuous lumen capable of receiving the dilator shaft, the lumen tapering from a proximal opening of the dilator centering device to a center portion of the dilator centering device, wherein the dilator centering device is separate from the dilator and from the sheath assembly, the sheath hub, and the sheath.

14. An apparatus as in claim 13, wherein the dilator centering device is engaged with the sheath assembly by a releasable locking mechanism.

15. An apparatus as in claim 14, wherein the releasable locking mechanism comprises:

an inner stem configured to fit into the sheath assembly; and
at least one flange around the inner stem configured to removably engage an outer surface of the sheath assembly.

16. An apparatus as in claim 14, wherein the dilator centering device is configured to come apart when a threshold force is applied to at least a proximal end of the dilator centering device.

17. An apparatus as in claim 14, wherein the dilator centering device is configured to engage the dilator hub by a locking mechanism.

18. An apparatus as in claim 17, wherein the locking mechanism is a circumferential groove on an outer surface of the dilator centering device.

19. An apparatus as in claim 13, wherein the dilator centering device is non-removably engaged with the sheath assembly.

20. An apparatus as in claim 13, further comprising a seal within the lumen and spanning at least a portion of the lumen.

21. An apparatus as in claim 13, wherein the seal is configured in at least one of: a funnel configuration, a spiral funnel configuration, a spiral double-funnel configuration, a multiple hinged flap configuration, and a multiple hinged spiral-flap configuration.

22. An apparatus as in claim 21, wherein the seal comprises at least three flaps.

23. A device as in claim 21, wherein the seal is a multiple hinged spiral-flap seal.

24. An apparatus, comprising:
a dilator comprising a dilator hub and a dilator shaft connected to the dilator hub;
a sheath assembly capable of receiving the dilator shaft, the sheath assembly comprising a sheath hub and a sheath; and
a dilator centering device engaged with the sheath assembly, the dilator centering device comprising a continuous lumen capable of receiving the dilator shaft and a valve, the lumen tapering from a proximal opening of the dilator centering device to a center portion of the dilator centering device, wherein the dilator centering device is separate from the dilator and from the sheath assembly, the sheath hub, and the sheath.

25. An apparatus, comprising:
a dilator comprising a dilator hub and a dilator shaft connected to the dilator hub;
a sheath assembly capable of receiving the dilator shaft, the sheath assembly comprising a sheath hub and a sheath; and
a dilator centering device engaged with the sheath assembly, the dilator centering device comprising a continuous channel capable of receiving the dilator shaft, the channel tapering from a proximal opening of the dilator centering device to a center portion of the dilator centering device, wherein the dilator centering device is separate from the dilator and from the sheath assembly, the sheath hub, and the sheath.

* * * * *